United States Patent [19]

Roberto et al.

[11] Patent Number: 5,071,855
[45] Date of Patent: Dec. 10, 1991

[54] PHARMACOLOGICALLY ACTIVE PIPERIDINYLIMIDAZOPYRIDINE COMPOUNDS

[75] Inventors: Giani Roberto; Parini Ettore; Borsa Massimiliano; Lavezzo Antonio, all of Milan, Italy

[73] Assignee: Dompé Farmaceutici SpA, Milan, Italy

[21] Appl. No.: 520,327

[22] Filed: May 7, 1990

[30] Foreign Application Priority Data

May 8, 1989 [IT] Italy .............................. 20404 A/89

[51] Int. Cl.$^5$ ................. C07D 471/04; A61K 31/435
[52] U.S. Cl. ..................................... 514/303; 546/118
[58] Field of Search ......................... 546/118; 514/303

[56] References Cited

FOREIGN PATENT DOCUMENTS 282133 9/1988 European Pat. Off. .

Primary Examiner—C. Warren Ivy
Assistant Examiner—Zinna Northington-Davis

Attorney, Agent, or Firm—Armstrong, Nikaido, Marmelstein, Kubovcik & Murray

[57] ABSTRACT

Novel 2-piperidinylimidazopyridines of the formula:

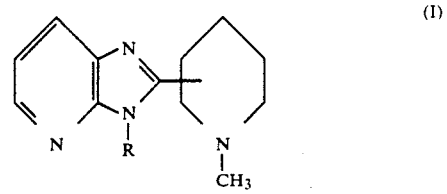

(I)

wherein R represents an alkoxyalkyl radical containing 4 to 6 carbon atoms; an optionally substituted benzyl radical or a tetrahydrofurfuryl radical as well as the non-toxic, pharmaceutically acceptable acid addition salts thereof.

The compounds of formula I are endowed with an interesting antihistaminic and antiallergic activity.

8 Claims, No Drawings

PHARMACOLOGICALLY ACTIVE PIPERIDINYLIMIDAZOPYRIDINE COMPOUNDS

The present invention relates to a new class of 2-piperidinyl substituted imidazopyridines which have an interesting antihistaminic and antiallergic activity, to their non-toxic, pharmaceutically acceptable acid addition salts with suitable acids, and to the process for their preparation.

More particularly the compounds of the present invention belong to the class of the formula:

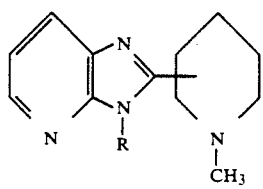

where R represents an alkoxyalkyl radical containing 4 to 6 carbon atoms, optionally substituted benzyl radical or tetrahydrofurfuryl radical The alkoxyalkyl radical can be represented by 2-ethoxyethyl, 2-propoxyethyl and propoxymethyl radical; among them 2-ethoxyethyl radical is preferred.

The benzyl radical optionally present in position 3 of the imidazopyridine ring can be substituted or unsubstituted; its suitable substituents are chlorine, fluorine, bromine, lower alkyl and lower alkoxyl. With the term lower, alkyl or alkoxy radicals containing in the molecule up to 4 carbon atoms are meant.

Suitable acids for the formation of pharmaceutically acceptable acid addition salts of compounds (I) can be organic and inorganic acids: among them fumaric, maleic, succinic and hydrochloric acid are preferred.

Fumaric acid is particularly preferred. Compounds of formula (I), when the imidazopyridine nucleus is bond to the piperidinyl radical in meta position, present an asymmetric centre of the piperidine carbon atom involved and therefore the relevant compound exists in racemic form as well as in form of the two separated enantioners.

Compounds of formula (I) are conveniently prepared starting from 2,3-diaminopyridine by reacting in warm conditions with a N-substituted piperidinecarboxylic acid and then reacting in warm conditions and the presence of sodium hydride the so-formed imidazopyridine with a suitable halide Hal R where R has the above mentioned meaning and Hal is a halogen atom, preferably chlorine and bromine.

Schematically the process can be represented as follows:

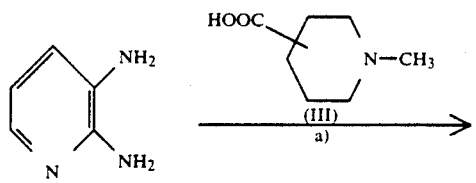

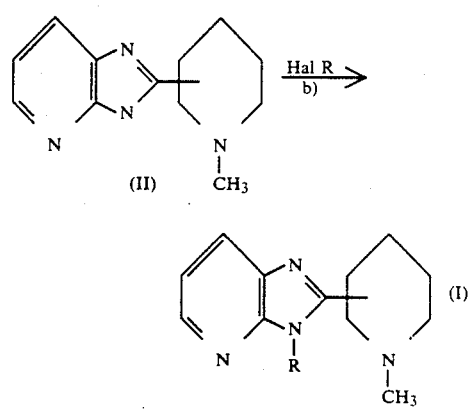

where Hal and R have the above mentioned meanings.

Reaction a) is carried out at high temperature, generally between 150°-220° C. without solvents, and piperidinecarboxylic acid (III) used is selected from the group consisting of N-substituted 3-piperidinecarboxylic acid and N-substituted 4-piperidinecarboxylic acid.

Reaction b) is also carried out in warm conditions, more particularly at a convenient temperature between 70°-120° C. and in the presence of a suitable organic solvent which is preferably constituted by N,N-dimethylformamide.

Compounds (I) can be usefully separated in form of non-toxic pharmaceutically acceptable acid addition salts with suitable organic and inorganic acids among which fumarate is particularly preferred.

Compounds (I) have demonstrated to possess an interesting antiallergic and antihistaminic activity. Such activities have been evaluated studying either the effect on the mortality induced by histamine and the effect on mortality induced by compound 48/80. Furthermore the effect on sleeping time and acute toxicity ($LD_{50}$) have been determined.

The methods followed in carrying out the above tests are here below described.

EFFECT ON THE MORTALITY INDUCED BY HISTAMINE

The method described by Romer D. et al. (Med. Welt. 17,791,1966) was followed and the tests were carried out on male albino guinea pigs (Dunkin-Hartley), weighing 350 to 450 g which were kept in cages with a grid floor, on an empty stomach for 24 hours with water ad libitum. The compounds under examination have been orally administered to the animals, dissolved in 0.5% carboxymethylcellulose, 60 minutes before intravenous administration of 1.25 mg/kg of histamine dihydrochloride in saline solution. In the control animals, treated with carboxymethylcellulose, the intravenous administration of histamine dihydrochloride induced a 100% mortality.

It has been evaluated $ED_{50}$, which corresponds to the amount of the compound able inhibit to 50% the mortality induced by histamine: estimation of $ED_{50}$ has been made applying the 'probit' method (Finney D. J. "Statistical method in biological assay", pg 512,1957).

MORTALITY INHIBITION BY COMPOUND 48/80

For evaluating the protection of the mortality induced by compound 48/80 administration the method described by C. J. E. Niemegeers et al. (Arch. Int. Pharmacodyn, 234,164,1978) was followed.

Sprague Dawley Nos male rats (Nossan, Correzzana, Milano) weighing 140 to 150 g, divided into groups of 10 animals each, on an empty stomach for 24 hours with water "ad libitum", were kept in cages with a grid floor, and treated intravenously with 2 mg/kg of compound 48/80 (1 ml/rat).

The animals were kept under observation for 4 hours taking note of their mortality. The results were expressed as the number of animals dead with respect to the number of treated animals. Compounds under examination or the carrier were administered 30 minutes before administration of compound 48/80 by intraperitoneal route, dissolved in $H_2O$ (5 ml/kg) or suspended in 0.5% carboxymethylcellulose. The experimental data were submitted to the variance analysis and to subsequent multiple comparisons according to Dunnet (D. J. Finney, in "Statistical Methods in Biological assay", Ed. L. Griffin and Co. Ltd., pag. 152,1957, Edition Ames Iowa, 1971).

EFFECT ON THE SLEEPING TIME INDUCED BY PENTOBARBITAL

The tests were carried out on male mice Swiss-Nos (Nossan, Correzzana, Milano) weighing 20-24 g, on an empty stomach for 18 hrs, according to the method described by R. Turner ("Screening Methods in Pharmacology", Acad. Press, pg 70,1965). The sleeping was induced by intraperitoneal administration of 40 mg/kg sodium pentobarbital. The narcosis start was considered from the moment when the animal, lying on its back, lost its straightening reflex. The narcosis end was considered from the moment when the animal recovered such reflex.

The carrier or the compounds under examination were intraperitoneally administered (25 mg/kg) 30 minutes before the pentobarbital administration.

The resulting data are expressed as sleeping time increase percent of the treated animals in comparison with the controls.

EVALUATION OF THE LETHAL DOSE$_{50}$ (LD$_{50}$)

Swiss Nos (Nossau, Correzzana, Milano) mice, weighing 18 to 20 g each, on an empty stomach for 18 hours with water "ad libitum" and kept in cages with grid floor, were used. The animals, divided into groups of 10 animals each, (5M+5F) were treated intraperitoneally (10 ml/kg) with the compounds under examination dissolved in water or suspended in 0.5% carboxymethyl-cellulose. The animals were kept in the cages and the mortality occurred within the following 6 hours was noted down. At the expiring of the 6 hours the animals were allowed to eat up to the end of the experimentation which lasted 14 days. During this period all the toxic symptoms and the mortality occuring were noted.

The animals which died during the test period and those which were sacrificed at the end of the same, underwent autopsy for a macroscopic examination of their main organs. The experimental data were statistically compared with the $X^2$ method and LD$_{50}$ was extrapolated by the 'probit' method.

The data resulting from the tests carried out on some significant compounds of the class (I), evaluated in comparison to the well known antihistaminic compound Terfenadine, are given in the following Table.

TABLE

| Compound | Mortality induced by hystamine ED$_{50}$ p.o. μg/kg | Mortality induced by 48/80 ED$_{50}$ i.p. μg/kg | Increase of sleeping time induced by pentobarbital 25 mg/kg increase % | Acute toxicity LD$_{50}$ i.p. mg/kg |
|---|---|---|---|---|
| Example 2 | 42 | 340 | 4 | 500 |
| Example 5 | 50 | 590 | 12 | <100 |
| Example 8 | 78 | N.D. | 16 | >100 |
| Terfenadine | 436 | 1990 | 44 | 620 |

For therapeutic administration, the compounds according to the present invention are used in the form of pharmaceutical preparations which contain said compounds in admixture with pharmaceutically acceptable carriers such as an organic or inorganic solid or liquid excipient suitable for oral or parenteral administration. The compounds of the invention may be contained in these pharmaceutical preparations in the form of free base or in the form of their non-toxic acid addition salts. The inorganic acids which may be employed to prepare these acid addition salts may be, e.g., hydrochloric or sulphuric acid. The organic acids which may be employed are, e.g., maleic, fumaric and succinic acid.

The pharmaceutical preparations may be in solid form as capsules, tablets, dragees or in liquid form such as solutions, suspensions or emulsions. If desired, there may be included in the above preparations auxiliary substances such as stabilizing agents and other commonly used additives, or there may be contained other therapeutically active agents suitable to be administered together with the compounds of the invention. The dosage of the compounds will vary from the administration route and will also depend upon the age and condition of the patient.

The following Examples have the purpose of illustrating the invention without limiting it.

EXAMPLE 1

3-(4-Fluorobenzyl)-2-(1-methylpiperidin-4-yl)-3H-imidazo[4,5-b] pyridine fumarate Grams 3.3 of 2,3-diaminopyridine and 5.4 g of N-methylisonipecotic acid hydrocloride are heated at 190° C. for 24 hours. The reaction mixture is cooled and diluted with a small amount of water then made alkaline to pH 10 by addition of NaOH then extracted several times with methylene chloride. The organic extracts are collected together and evaporated to dryness. The residue, crystallized from acetonitrile, gives 2 g (31% of the theoretical value) 2-(1-methylpiperidin-4-yl)-3H-imidazo [4,5-b] pyridine melting at 224°-226° C. To a solution constituted by 3 g 2-(1-methylpiperidin-4-yl)-3H-imidazo[4,5-b] pyridine in 10 ml N,N-dimethylformamide 0.6 g 60% sodium hydride are added in portions and subsequently, dropwise, a solution constituted by 1.7 ml p-fluorobenzylchloride in 2 ml N,N-dimethylformamide. The reaction mixture is heated to 100° C. for 2 hours, then cooled and 30 ml water are added thereto. Extraction with diethylether is repeated several times, the ethereal extracts are collected together and evaporated to dryness. The residue product, consisting of 1.1 g 3-(4-fluorobenzyl)-2-(1-methylpiperidin-4-yl)-3H-imidazo [4,5-b] pyridine is isolated as fumarate melting at 242°-245° C. (ethyl alcohol).

EXAMPLE 2

3-(2-Ethoxyethyl)-2-(1-methylpiperidin-4-yl)-3H-imidazo [4,5-b] pyridine 1.5 fumarate Operation is carried out similarly to the above description with the difference that 2-(1-methylpiperidin-4-yl)-3H-imidazo [4,5-b] pyridine is reacted with 2-ethoxyethyl chloride to obtain 3-(2-ethoxyethyl)-2-(1-methylpiperidin-4-yl)-3H-imidazo [4,5-b] pyridine which is isolated as hemitrifumarate melting at 157°-158° C. (ethyl alcohol).

EXAMPLE 3

3-Tetrahydrofurfuryl-2-(1-methylpiperidin-4-yl)-3H-imidazo[4,5-b] pyridine difumarate Operation is carried out similarly to the above description with the difference that 2-(1-methylpiperidin-4-yl)-3H-imidazo [4,5-b] pyridine is reacted with tetrahydrofurfurylbromide to obtain 3-tetrahydrofurfuryl-2-(1-methylpiperidin-4-yl)-3H-imidazo [4,5-b] pyridine which is isolated as difumarate melting at 154°-156° C. (ethyl alcohol).

EXAMPLE 4

3-Benzyl-2-(1-methylpiperidin-4-yl)-3H-imidazo [4,5-b] pyridine fumarate.

Operation is carried out similarly to the above description with the difference that 2-(1-methylpiperidin-4-yl)-3H-imidazo-[4,5-b] pyridine is reacted with benzylchloride to obtain 3-benzyl-2-(1-methylpiperidin-4-yl)-3H- imidazo-[4,5-b] pyridine which is isolated as fumarate melting at 205°-207° C. (ethyl alcohol).

EXAMPLE 5

3-(2-Ethoxyethyl)-2-(1-methylpiperidin-3-yl)-3H-imidazo [4,5-b] pyridine difumarate Grams 10.9 of 2,3-diaminopyridine and 17,9 g N-methylnipecotic acid hydrochloride are heated at 190° C. for 6 hours. The reaction mixture is cooled and diluted with a small amount of water, then is made alkaline to pH 10 by addition of NaOH and extraction is repeated several times with methylene chloride. The organic extracts, collected together, are evaporated to dryness. The obtained residue, is extracted several times with diethyl ether and the ethereal extracts are evaporated to dryness. The obtained residue, crystallized from acetonitrile, provides 5 g (23% of the theoretical value) 2-(1-methylpiperidin-3-yl)-3H-imidazo-[4,5-b] pyridine melting at 141°-144° C.

To a solution constituted by 2.5 g 2-(1-methylpiperidin-3-yl)-3H-imidazo-[4,5-b] pyridine in 5 ml N,N-dimethylformamide, 0.5 g of 60% sodium hydride are added in portions, and subsequently a solution of 1.3 g 2-ethoxyethylchloride in 2 ml N,N-dimethylformamide is added dropwise thereto. The reaction mixture is heated to 100° C. for 4 hours, then cooled and a small amount of water is added thereto.

Extraction with diethyl ether is carried out several times and the ethereal extracts are collected together and evaporated to dryness. The residue product, consisting of 2.4 g 3-(2-ethoxyethyl)-2-(1-methylpiperidin-3-yl)-3H-imidazo [4,5-b] pyridine, is isolated as difumarate melting at 130°-133° C. (acetonitrile).

EXAMPLES 6 AND 7

R(−)3-(2-Ethoxyethyl)-2-(1-methylpiperidin-3-yl)-3H-imidazo[4,5-b] pyridine difumarate

S(+)3-(2-Ethoxyethyl)-2-(1-methylpiperidin-3-yl)-3H-imidazo[4,5-b] pyridine difumarate Operation is carried out similarly to the above description of Example 5 starting from R(−) N-methylnipecotic acid hydrochloride or from S(+)N-methylnipecotic acid hydrochloride and R(−)3-(2-ethoxyethyl)-2-(1-methylpiperidin-3-yl)-3H-imidazo [4,5-b] pyridine difumarate, and S(+)-3-(2-ethoxyethyl)-2-(1-methylpiperidin-3-yl)-3H-imidazo [4,5-b] pyridine difumarate are obtained respectively.

EXAMPLE 8

3-Benzyl-2-(1-methylpiperidin-3-yl)-3H-imidazo [4,5-b] pyridine

Operation is carried out similarly to the description of Example 5 with the difference that 2-(1-methylpiperidin-3-yl)3H-imidazo [4,5-b] pyridine is reacted with benzylchloride to obtain 3-benzyl-2-(1-methylpiperidin-3-yl)-3H-imidazo [4,5-b] pyridine as an oil, after purification by chromatography on silicagel column (CHCl₃-CH₃OH 9:1).

| Yield 44% - Elementar analysis for $C_{19} H_{22} N_4$. | | | |
|---|---|---|---|
| | C | H | N |
| calculated % | 74.48 | 7.24 | 18.28 |
| found % | 74.81 | 7.21 | 18.12 |

EXAMPLES 9 AND 10

S(+)3-Benzyl-2-(1-methylpiperidin-3-yl)-3H-imidazo [4,5-b] pyridine

R(−)3-Benzyl-2-(1-methylpiperidin-3-yl)-3H-imidazo [4,5-b] pyridine

Operation is carried out similarly to the above description of Example 8 starting from S(+)N-methylnipecotic acid hydrochloride or from R(−)N-methylnipecotic acid hydrochloride to obtain S(+)3-benzyl-2-(1-methylpiperidin-3-yl)-3H-imidazo [4,5-b] pyridine and R(−)-3-benzyl-2-(1-methylpiperidin-3-yl)3H-imidazo [4,5-b] pyridine respectively.

We claim:

1. A 2-Piperidinylimidazo [4,5-b] pyridine of formula:

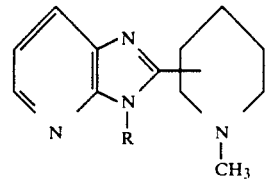

where
R represents an alkoxyalkyl radical containing 4 to 6 carbon atoms, benzyl radical optionally substituted with a halogen atom, with an alkyl or alkoxyalkyl radical containing 1 to 4 carbon atoms or a tetrahydrofurfuryl radical or
a non-toxic pharmaceutically acceptable acid addition salt thereof.

2. A 2-Piperidinylimidazo [4,5-b] pyridine of formula:

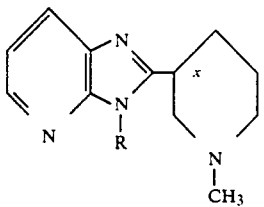

where the asterisk indicates an asymmetric carbon atom and
R represents an alkoxyalkyl radical containing 4 to 6 carbon atoms, a benzyl radical optionally substituted with a halogen atom, with an alkyl or alkoxyalkyl radical containing 1 to 4 carbon atoms, or a tetrahydrofurfuryl radical, as separated enantioners or a mixture thereof; or
a non-toxic, pharmaceutically acceptable acid addition salt thereof.

3. A 2-Piperidinylimidazo [4,5-b] pyridine according to claims 1 or 2, wherein R represents the 2-ethoxyethyl radical.

4. 3-(2-Ethoxyethyl)-2-(1-methylpiperidin-4-yl)-3H-imidazo [4,5-b] pyridine 1.5 fumarate.

5. 3-(2-Ethoxyethyl)-2-(1-methylpiperidin-3-yl)-3H-imidazo [4,5-b] pyridine difumarate.

6. A 2-Piperidinylimidazo [4,5-b] pyridine according to claims 1 or 2, wherein R represents an optionally substituted benzyl radical.

7. 3-Benzyl-2-(1-methylpiperidin-3-yl)-3H-imidazo [4,5-b] pyridine.

8. A pharmaceutical composition comprising an antihistaminically effective amount of at least one compound according to any one of claims 1, 2, 4, 5 and 7 in admixture with a pharmaceutically acceptable carrier.

* * * * *

UNITED STATES PATENT AND TRADEMARK OFFICE
CERTIFICATE OF CORRECTION

PATENT NO. : 5,071,855
DATED : December 10, 1991
INVENTOR(S) : Roberto GIANI et al It is certified that error appears in the above-identified patent and that said Letters Patent is hereby corrected as shown below:

On the cover page, Item [75], the inventors' names should read as follows:

-- Roberto GIANI; Ettore PARINI; Massimiliano BORSA; Antonio LAVEZZO --.

Item [19], "Roberto" should be changed to read --Giani--.

Signed and Sealed this

Twenty-seventh Day of April, 1993

Attest:

MICHAEL K. KIRK

*Attesting Officer*  *Acting Commissioner of Patents and Trademarks*